(12) United States Patent
Hirabuki (10) Patent No.: US 7,566,315 B2
(45) Date of Patent: Jul. 28, 2009

(54) BLOOD COMPONENT COLLECTION APPARATUS AND METHOD

(75) Inventor: Makoto Hirabuki, Shizuoka (JP)

(73) Assignee: Terumo Kabushiki Kaisha, Tokyo (JP)

( * ) Notice: Subject to any disclaimer, the term of this patent is extended or adjusted under 35 U.S.C. 154(b) by 316 days.

(21) Appl. No.: 11/453,840

(22) Filed: Jun. 16, 2006

(65) Prior Publication Data

US 2006/0287628 A1 Dec. 21, 2006

(30) Foreign Application Priority Data

Jun. 17, 2005 (JP) .............................. 2005-178316

(51) Int. Cl.
*A61M 37/00* (2006.01)
(52) U.S. Cl. ...................... 604/6.01; 604/6.07; 604/6.15
(58) Field of Classification Search ....... 604/6.01–6.05, 604/6.07, 6.11, 6.15, 6.16
See application file for complete search history.

(56) References Cited

U.S. PATENT DOCUMENTS

| | | | | |
|---|---|---|---|---|
| 4,197,847 A | * | 4/1980 | Djerassi | ..................... 604/6.02 |
| 4,416,654 A | * | 11/1983 | Schoendorfer et al. | ........ 494/10 |
| 5,437,624 A | * | 8/1995 | Langley | ..................... 604/6.05 |
| 5,494,592 A | | 2/1996 | Latham, Jr. et al. | |
| 5,607,579 A | | 3/1997 | Latham, Jr. et al. | |
| 6,296,450 B1 | * | 10/2001 | Westberg et al. | .............. 417/18 |
| 6,723,062 B1 | * | 4/2004 | Westberg et al. | .......... 604/4.01 |
| 6,849,039 B2 | | 2/2005 | Min et al. | |
| 2004/0112808 A1 | | 6/2004 | Takagi et al. | |
| 2006/0178612 A9 | * | 8/2006 | Vandlik et al. | ............. 604/6.03 |

FOREIGN PATENT DOCUMENTS

JP 2005-199055 7/2005

* cited by examiner

*Primary Examiner*—Tatyana Zalukaeva
*Assistant Examiner*—Susan Su
(74) *Attorney, Agent, or Firm*—Buchanan Ingersoll & Rooney, P.C.

(57) ABSTRACT

A blood component collection apparatus comprises a blood component collecting circuit which includes an anticoagulant line for feeding an anticoagulant and a line for collecting an initial flow of collected blood. In the blood component collection apparatus, air is intermediately present between the anticoagulant and the blood in the passage of a blood collection needle side line, after a priming operation is performed in which anticoagulant is supplied from the anticoagulant line toward the side of a centrifugal separator in the blood collection needle side line through a branch connector and after an initial flow collecting operation is performed in which the initial flow of blood is collected.

13 Claims, 3 Drawing Sheets

FIG. 3

BLOOD COMPONENT COLLECTION APPARATUS AND METHOD

FIELD OF THE INVENTION

The present invention generally relates to the collection of blood components. More particularly, the invention pertains to blood a blood component collection apparatus and a method of collecting blood or operating a blood collection apparatus.

BACKGROUND DISCUSSION

Blood component collection involves separating blood (whole blood) collected from a donor into blood components by centrifugal separation or membrane separation, collecting a required blood component or components, and returning the other blood components to the donor. In blood component collection utilizing a centrifugal separation system, particularly a centrifugal bowl system, a single blood collection needle is used, and a blood collection step and a blood return step are alternately repeated for the purpose of reducing the invasiveness to the donor. Examples of this type of system are described in U.S. Pat. No. 5,494,592 and U.S. Pat. No. 5,607,579.

In typical blood component collection, a needle-piercing portion of the donor is sterilized with alcohol. However, there is a possibility that bacteria present on the skin or subcutaneously can enter the blood component collecting bag together with the blood component.

Some kind of bacteria which have entered the blood collecting bag increase while the blood collecting bag is kept cold. When the blood is transfused into a patient, the patient may suffer from infectious disease or blood poisoning.

The pH of red blood cell conservation liquid (S.A.GM. liquid, OPTISOL liquid, M.A.P. liquid, and the like) currently used is substantially neutral, unlike the conventional blood conservation liquid (anticoagulants such as ACD-A liquid and CPD liquid). Thus, in the red blood cell conservation liquid, bacteria can increase to a high extent while the blood collecting bag is refrigerated.

Because the bacteria are present not only on the skin but also under the skin, careful sterilization of the needle-piercing portion only is not sufficient to prevent them from penetrating into blood.

It is experimentally known that bacteria penetrates into an initial flow of collected blood, together with fragments of skin.

However, a blood collecting device capable of removing the initial flow of collected blood has not been developed.

SUMMARY

The apparatus and method disclosed herein makes it possible to prevent the collected blood or blood component from being infected with bacteria, to enhance safety, and to prevent anticoagulant from mixing into the initial flow of the collected blood.

A blood component collection apparatus for separating blood from a donor so as to collect a predetermined blood component comprises a blood collection needle for collecting blood from a donor, a blood separator for separating the predetermined blood component from the blood collected by the blood collection needle, a blood component collecting circuit, and supply means for adding anticoagulant to the blood collected by the blood collection needle. The blood component collecting circuit comprises a blood component collecting bag for collecting the predetermined blood component separated by the blood separator, a blood line connecting the blood collection needle and an inflow port of the blood separator, an anticoagulant feeding line branched from a first branched portion of the blood line to feed an anticoagulant, and an initial flow collecting line branched from the second branched portion to collect a initial flow of the blood collected from the donor. An air containing space is intermediately present between the anticoagulant and the blood in a passage of the blood line after both a priming operation is performed in which the anticoagulant is supplied from the anticoagulant feeding line toward a blood separator side of the blood line through the first branched portion by operating the supply means and an initial flow collecting operation is performed in which the initial flow of the blood is supplied to the initial flow collecting line.

According to another aspect, a blood component collection apparatus for separating blood from a donor so as to collect a predetermined blood component comprises a blood collection needle for collecting blood from a donor, a blood separator which separates the predetermined blood component from the blood collected by the blood collection needle, a blood component collecting bag for collecting the predetermined blood component separated by the blood separator, and a blood line connecting the blood collection needle and an inflow port of the blood separator. The blood line is provided with a first branched portion and a second branched portion, with the second branched portion being positioned between the blood collection needle and the first branched portion. In addition, an anticoagulant feeding line is provided to feed anticoagulant and has one end branching from the first branched portion of the blood line, and an initial flow collecting line has one end branching from the second branched portion. The first and second branched portions of the blood line are spaced apart from one another to provide an air space in the blood line between the anticoagulant and the blood in the blood line after a priming operation is performed in which the anticoagulant is supplied into the blood line through the anticoagulant feeding line and the first branched portion and after an initial flow collecting operation is performed in which the initial flow of the blood from the donor is supplied to the initial flow collecting line through the blood line and the first branched portion.

Another aspect involves a method for collecting a blood component using a blood component collection apparatus which separates a predetermined blood component from blood collected from a donor so as to collect a predetermined blood component. The blood component collection apparatus used in the method comprises a blood collection needle for collecting blood from the donor, a blood separator for separating the predetermined blood component from the blood collected from the donor by the blood collection needle, a blood component collecting bag for collecting the predetermined blood component separated by the blood separator, a blood line connecting the blood collection needle and an inflow port of the blood separator, an anticoagulant feeding line branched from a first branch portion provided in the blood line to feed an anticoagulant, an initial flow collecting line to collect a initial flow of the blood collected from the donor, wherein the initial flow collecting line branches from a second branch portion provided in the blood line between the blood collection needle and the first branch portion, and supply means for supply the anticoagulant to the blood collected by the blood collection needle. The method comprises priming the blood line toward a blood separator side of the blood line through the anticoagulant feeding line and the first branched portion by supplying the anticoagulant through operation of the supply means to fill the blood line with the anticoagulant from the anticoagulant feeding line and the first branched portion toward a proximal side of the blood separator, and collecting an initial flow of the blood from the donor by way of the collection needle through the second branched portion and the initial flow collecting line after the priming, with air being intermediately present in a passage of the blood line between the anticoagulant and the initial flow of the blood collected from the donor.

Another aspect involves a method for operating a blood component collection apparatus which comprises a blood collection needle for collecting blood from the donor, a blood separator for separating a predetermined blood component from the blood collected from the donor by the blood collection needle, a blood line connecting the blood collection needle to the blood separator; a first branched portion provided along the blood line; a second branched portion provided along the blood line between the blood collection needle and the first branched portion; and an initial flow collecting line branching from the second branch portion. The method comprises supplying anticoagulant into the blood line by way of the first branched portion to prime the blood line toward the blood separator, and supplying an initial flow of the blood from the collection needle through the second branched portion and into the initial flow collecting line after the blood line is primed, with air present in the blood line between the anticoagulant and the initial flow of the blood.

Since the initial flow collecting line is provided, the initial flow of the blood collected (collected initiate blood flow) which is highly probably infected with bacteria can be easily collected (removed) at the time of blood collecting. This helps ensure that mixing of bacteria into the blood collected or into the blood component(s) separated from the collected blood is restrained so that safety is thereby enhanced.

In addition, since the air layer is formed or is intermediately present between the collected initiate blood flow (blood) and the anticoagulant in the passage of the blood line after the priming operation and the initial flow collecting operation are performed, the contact between the collected initiate blood flow and the anticoagulant is inhibited by the air layer, and mixing of the anticoagulant into the collected initiate blood flow can be prevented. This helps ensure that the collected initiate blood flow thus collected (sampled) can be used as blood to be tested.

Also, because the contact between the collected initiate blood flow and the anticoagulant is inhibited, mixing of the collected initiate blood flow into the anticoagulant can be avoided or prevented. This makes it possible to prevent bacteria from mixing into the blood component collected into the blood component collecting bag.

Further, where the air layer is transferred from the blood line into the initial flow collecting line by performing an anticoagulant supplying operation after the priming operation and the initial flow collecting operation are performed, it is possible to obviate the possibility that the blood not containing the anticoagulant might stagnate in the initial flow collecting line or in the branch portion for branching the initial flow collecting line from the blood line (blood collecting line) and might coagulate there. This makes it possible for blood component collection to be performed safely and assuredly, without increasing the burden on the donor.

DETAILED DESCRIPTION

Figure 1:
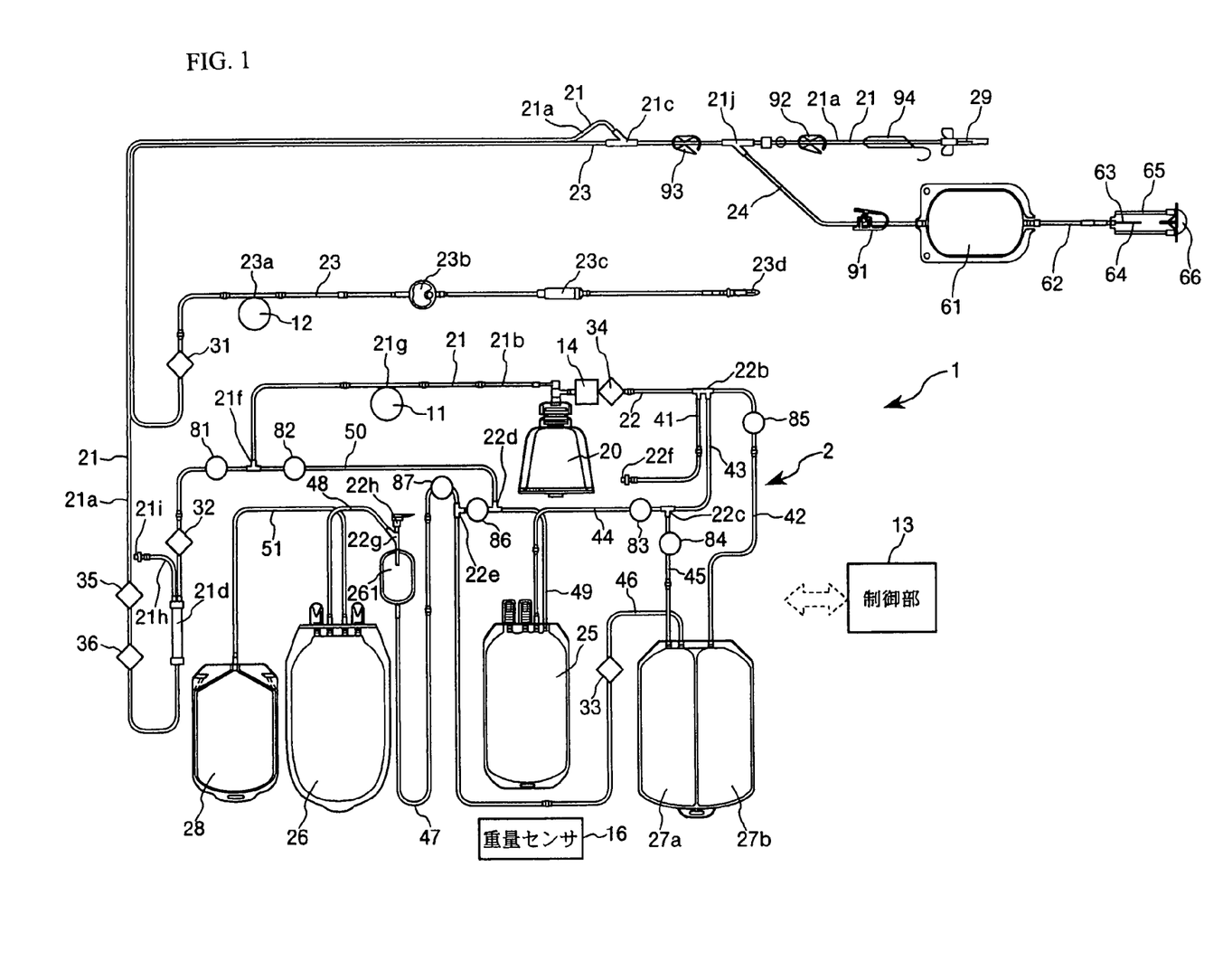
FIG. 1 is a plan view showing an embodiment of a blood component collection apparatus described herein.
Figure 2:
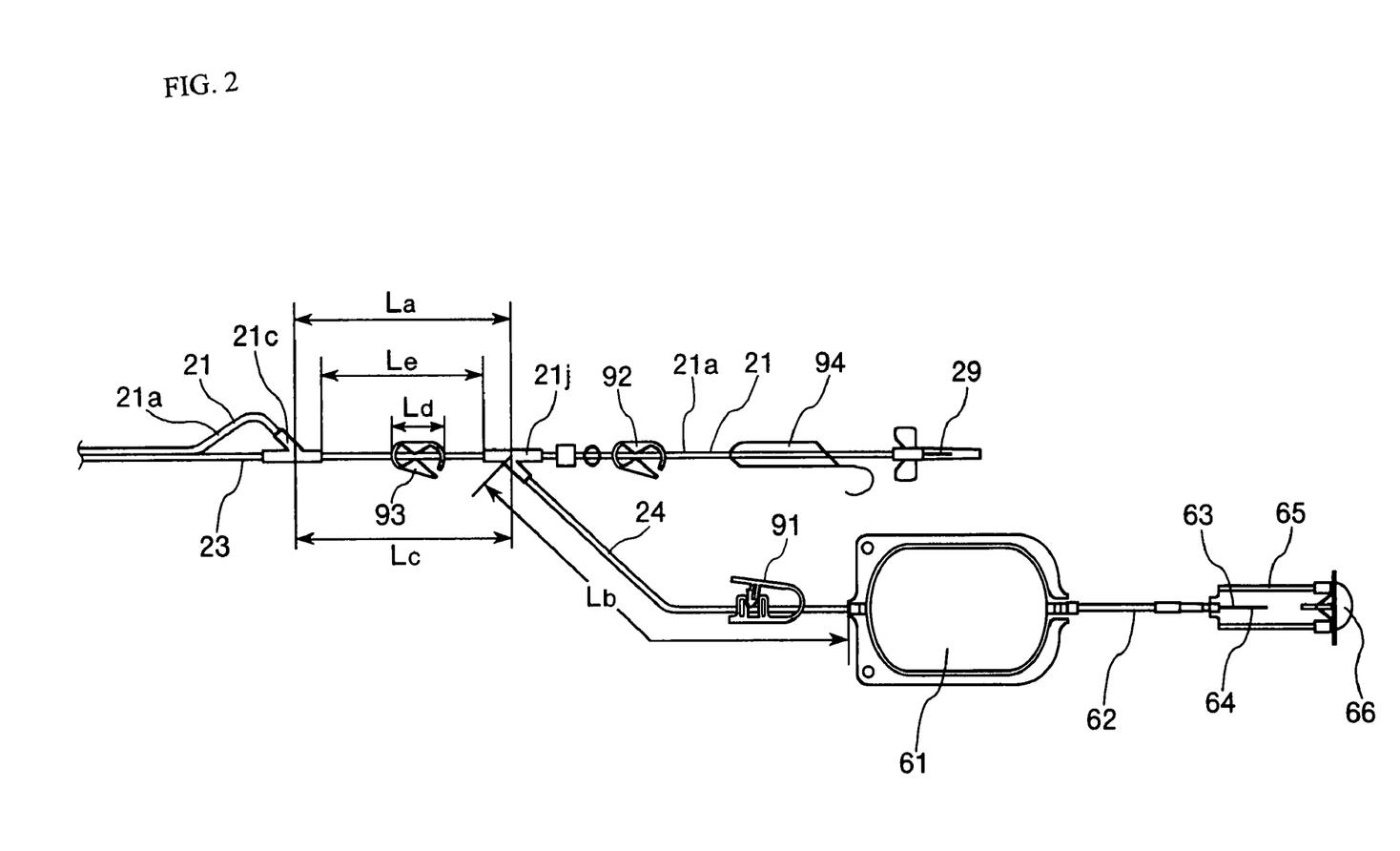
FIG. 2 is a partly cutaway sectional view showing the state wherein a centrifugal separator is mounted onto a centrifugal separator drive unit provided in the blood component collection apparatus shown in FIG. 1.

The blood component collection apparatus 1 shown in FIG. 1 is a system for separating a plurality of components of blood and for collecting the separated blood components. In this disclosed embodiment, the separated blood components to be collected include platelets (the platelet concentrate) (blood component) and plasma (blood component). The blood component collection apparatus 1 comprises a centrifugal separator (blood separator) 20 and a blood component collecting circuit (collecting circuit) 2. As generally shown in FIG. 2, the centrifugal separator 20 includes a rotor 142 having a blood reserving space 146 therein, and an inflow port (inlet) 143 and a discharge port (outflow port or outlet) 144 both of which communicate with the blood reserving space 146, and carries out centrifugal separation in the blood reserving space 146 by the rotation of the rotor 142. The blood component collecting circuit 2 includes a first line (blood line) 21 connecting a blood collection needle 29 and the inflow port 143 of the centrifugal separator 20 to each other, a second line 22 connected to the discharge port 144 of the centrifugal separator 20, a third line 23 (anticoagulant feeding line) and a fourth line 24 (initial flow removing line or initial flow collecting line) both connected to the first line 21, a plasma collecting bag (blood component collecting bag) 25 connected to the first line 21 through tubes 49, 50 and connected to the second line 22 through tubes 43, 44, an air bag 27b connected to the second line 22 through a tube 42, an intermediate bag (temporarily reserving bag) 27a connected to the second line 22 through tubes 43, 45, a platelet collecting bag (blood component collecting bag) 26 connected to the intermediate bag 27a through tubes 46, 47, 48, a bag 28 connected to the platelet collecting bag 26 through a tube 51, and a initial flow collecting bag 61 connected to the fourth line 24.

Furthermore, the blood component collection apparatus 1 comprises a centrifugal separator drive unit 10, shown in FIG. 2, for rotating the rotor 142 of the centrifugal separator 20, a first liquid feed pump 11 for the first line 21, a second liquid feed pump (supply means) 12 for the third line 23, a plurality of passage opening/closing devices 81, 82, 83, 84, 85, 86, 87 (passage opening/closing means) adapted to open and close the passages of the blood component collecting circuit 2, a control unit (control means) 13 for controlling the centrifugal separator drive unit 10, the first liquid feed pump 11, the second liquid feed pump 12 and the plurality of passage opening/closing devices 81-87, a turbidity sensor 14, an optical sensor 15, a weight sensor 16, and a plurality of bubble sensors 31, 32, 33, 34, 35, 36. In the illustrated embodiment, the plurality of passage opening/closing devices are seven in number, thus comprising first to seventh passage opening/closing device, and the plurality of bubble sensor are six in number.

The blood component collecting circuit 2 includes: the first line (blood collecting and returning line) 21 which connects the blood collection needle 29 for collecting blood from a donor and the inflow port 143 of the centrifugal separator 20 to each other and has a first pump tube 21g; the second line 22 connected to the discharge port (outflow port) 144 of the centrifugal separator 20 on one end side thereof; the third line (anticoagulant feeding line) 23 having a second pump tube 23a and connected to the first line 21 at a position in the vicinity of the blood collection needle 29; the fourth line (initial flow removing line or initial flow collecting line) 24 connected to a portion of the first line 21 between the blood collection needle 29 and the connection portion at which the third line 23 is connected to the first line 21; the tube 50 connected to a portion of the first line 21, on the blood collection needle 29 side relative to the first pump tube 21g; the tube 49 connected to the tube 50; the tube 43 connected to the second line 22; the tube 44 connected to the tube 43; the plasma collecting bag 25 connected to the tubes 44, 49; the tube 42 connected to the second line 22; the air bag 27b connected to the tube 42; the tube 45 connected to the tube 43; the intermediate bag 27a connected to the tube 45; the tube 46 connected to the intermediate bag 27a; the tube 47 connected to the tube 46; the tube 48; the platelet collecting bag 26 connected to the tube 48; the tube 51 connected to the platelet collecting bag 26; the bag 28 connected to the tube 51; and the initial flow collecting bag 61 connected to an end portion of the fourth line 24. The air bag 27b and the intermediate bag 27a are formed integrally with one another as a united unit.

The first line 21 includes a blood collection needle side first line 21a to which the blood collection needle 29 is connected, and a centrifugal separator side first line 21b which is connected to the blood collection needle side first line 21a on one end side thereof and is connected to the inflow port 143 of the centrifugal separator 20 on the other end side thereof. By way of example, a known metallic needle can be used as the blood collection needle 29. The blood collection needle 29 constitutes a primary part of a blood collecting means.

The blood collection needle side first line 21a, the centrifugal separator side first line 21b, the second line 22, the third line 23, and the fourth line 24 are each composed of a soft resin-made tube (tube) or a plurality of soft resin-made tubes (tubes) connected to each other. Additional details about the second thru fourth lines will be described below.

Figure 3:
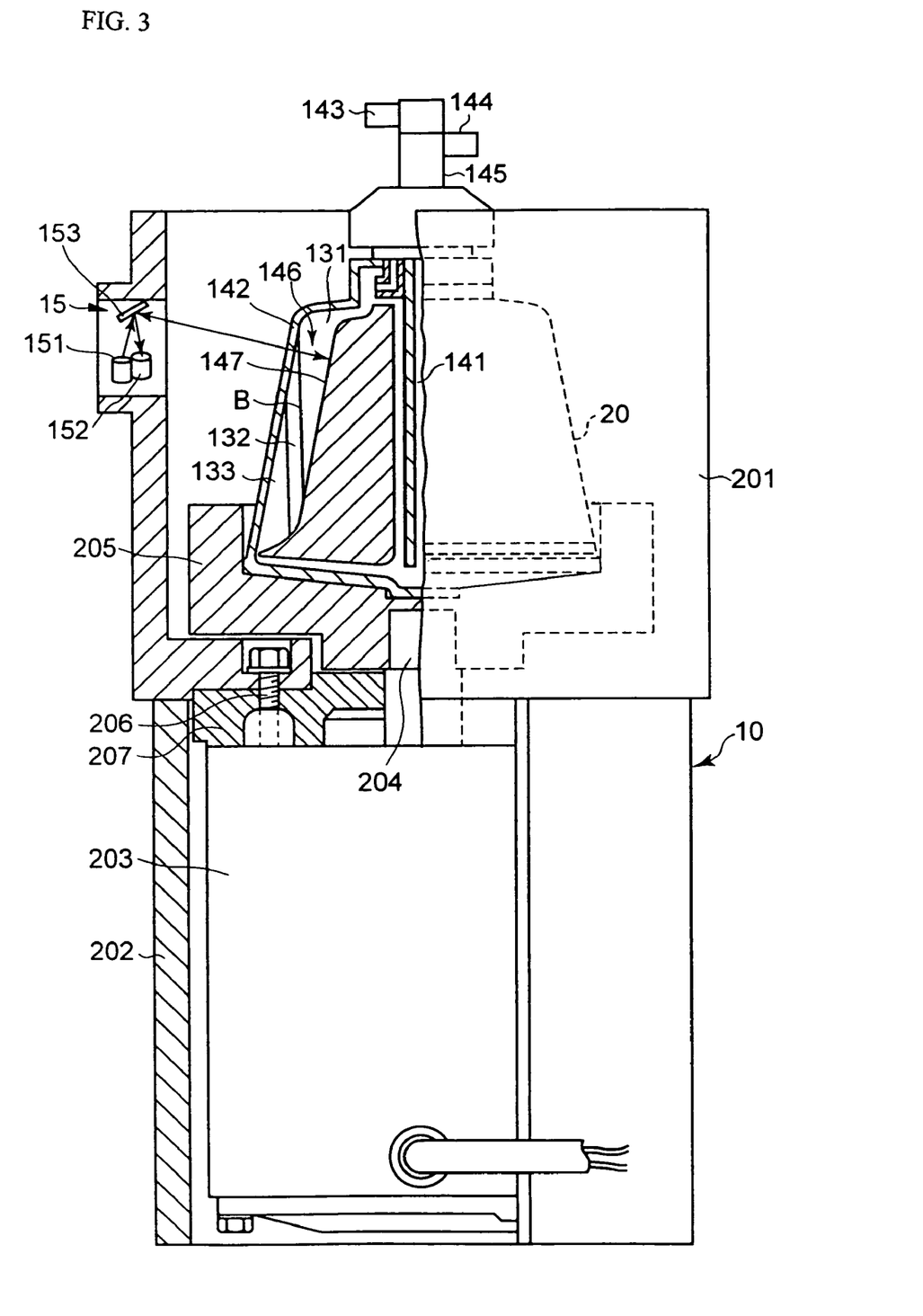
FIG. 3 is a plan view showing a blood collection needle side first line, fourth line and other features of the blood component collection apparatus shown in FIG. 1.

The blood collection needle side first line 21a includes a branch connector 21c for connection with the third line 23, a chamber 21d for removal of bubbles and microaggregates, and a branch connector 21f for connection with the tube 50 which are arranged in this order from the blood collection needle 29 side.

Bubble sensors (detection means) 35, 36, 32 are disposed along the blood collection needle side first line 21a, in this order from the blood collection needle 29 side. In the illustrated embodiment, the bubble sensors 35, 36 are arranged between the branch connector 21c and the chamber 21d, while the bubble sensor 32 is arranged between the chamber 21d and the branch connector 21f.

The bubble sensors 35, 36, 32 function as detection means adapted to detect a gas and a liquid (e.g., gas/liquid distinction or gas/liquid interface) in a tube by transmitting and receiving ultrasound on the outside of the tube and utilizing the difference between a liquid and a bubble (gas) in ultrasound conductivity. It is to be noted that the bubble sensors 31, 33, 34 are also detection means having the same function as just-mentioned. The bubble sensors (gas and liquid detection means) are not limited to the ultrasound-type sensor just mentioned. For example, as the bubble sensors, an optical sensor, an IR sensor, or the like may also be used.

The chamber 21d is connected with a gas-permeable and bacteria-impermeable filter 21i via a tube 21h. This line can be used, for example, for detecting the pressure inside the blood collection needle side first line 21a.

The centrifugal separator side first line 21b is connected to the branch connector 21f for connection with the tube 50. The first pump tube 21g is formed or positioned at an intermediate portion of the centrifugal separator side first line 21b.

The second line 22 is connected to the discharge port 144 of the centrifugal separator 20 on one end side thereof. The second line 22 includes a branch connector 22b for connection with the tubes 42, 43.

The turbidity sensor 14 and a bubble sensor 34 are disposed, in this order from the centrifugal separator 20 side, along the second line 22. In this case, the turbidity sensor 14 and the bubble sensor 34 are arranged between the centrifugal separator 20 and the branch connector 22b.

A gas-permeable and bacteria-impermeable filter 22f is connected to the branch connector 22b through a tube 41. This line can be used, for example, for detecting the pressure inside the second line 22.

The third line 23 is connected at its one end to the branch connector 21c provided in the first line 21. Specifically, the third line (passage) 23 branches from the branch connector (first branch portion) 21c, i.e., is branched from the first line or first passage 21 through the branch connector 21c. In addition, the branch connector 21c is located or provided in the vicinity of the blood collection needle 29.

The third line 23 is provided with a second pump tube 23a, a bacteria removing filter (foreign matter removing filter) 23b, a bubble removing filter 23c, and an anticoagulant container connecting needle 23d, arranged in this order from the branch connector 21c side.

In addition, a bubble sensor 31 is disposed along the third line 23. The bubble sensor 31 is arranged between the branch connector 21c and the second pump tube 23a.

The anticoagulant container connecting needle 23d in the third line 23 is connected to a container (not shown) for storing (containing) an anticoagulant (anticoagulant liquid). The anticoagulant in the container flows through the third line 23 from the anticoagulant container connecting needle 23d toward the branch connector 21c, to be supplied or fed into the blood collection needle side first line 21a, as will be described later. This ensures that the anticoagulant can be added to or mixed into the blood collected through the blood collection needle 29, via the third line 23, for example.

The anticoagulant is not particularly limited. By way of example, an ACD-A liquid or the like can be used.

The fourth line 24 is connected at its one end to a branch connector 21j provided in the first line 21. Specifically, the fourth line or fourth passage 24 is branched from the branch connector (second branch portion) 21j, i.e., is branched from the first line or first passage 21 through the branch connector 21j. In addition, the branch connector 21j is located or provided between the blood collection needle 29 and the branch connector 21c.

The initial flow collecting bag (fourth container) 61 is a container for collecting (reserving) an initial flow of the blood collected from a donor through the blood collection needle 29 (collected initiate blood flow). The other end of the fourth line 24 is connected to the initial flow collecting bag 61.

The inside volume of the initial flow collecting bag 61 is not particularly limited, but is preferably about 10 to 100 mL, more preferably 25 to 50 mL.

If the inside volume of the initial flow collecting bag 61 is less than this range, it may be difficult or impossible to sufficiently remove or collect the initial flow of the blood collected from the donor through the blood collection needle 29 (collected initiate blood flow). On the other hand, if the inside volume of the initial flow collecting bag 61 is in excess of the range, the blood component collection apparatus 1 (blood component collecting circuit 2) would be quite large in size.

One end of a tube 62 is connected to the side of the initial flow collecting bag 61 that is opposite the connection portion of the fourth line 24 to the initial flow collecting bag 61. A needle pipe 63 is connected to the other end of the tube 62.

An envelope member 64 for enveloping the needle pipe 63 is disposed in surrounding relation to the needle pipe 63. The envelope member 64 is composed, for example, of a film of one of various rubber materials (elastic materials), preferably, a material which can be easily pierced by the needle tip of the needle pipe 63.

In addition, a holder 65 fitted with a cap 66 is detachably attached to the base end side of the needle pipe 63, whereby the needle pipe 63 is housed in the holder 65.

Clamps forming passage opening/closing devices (passage opening/closing means) 91, 92, 93 and adapted to open and close an intermediate portion of a line (passage) are provided respectively at an intermediate portion of the fourth line 24, at a portion of the blood collection needle side first line 21a between the blood collection needle 29 and the branch connector 21j, and at a portion of the blood collection needle side first line 21a between the branch connector 21j and the branch connector 21c. The clamp (first clamp) 91 is provided for opening and closing the passage (passage inside the tube) of the fourth line 24. The clamp (second clamp) 92 is provided for opening and closing the passage (passage inside the tube) of the blood collection needle side first line 21a between the blood collection needle 29 and the branch connector 21j. The clamp (third clamp) 93 is provided for opening and closing the passage (passage inside the tube) of the blood collection needle side first line 21a between the branch connector 21j and the branch connector 21c.

Here, when the clamp 91 is once closed in a blood component collecting operation, the clamp 91 will not be opened again. Therefore, a clamp (passage closing means) which cannot be opened (or is difficult to open) after it has once been closed, for example a shutter clamp, is preferably used as the clamp 91. In this embodiment, a shutter clamp is used as the clamp 91.

It is to be understood that other devices may be used in place of the clamps. For example, forceps or the like may be used in place of the clamps 91, 92, 93.

In the condition where the clamps 91, 92 are opened and the clamp 93 is closed, the initial flow of blood collected from the donor through the blood collection needle 29 flows from the blood collection needle 29 through the blood collection needle side first line 21a, the branch connector 21j and the fourth line 24, under the venous blood pressure of the donor and/or the head (gravity), and is introduced into or collected in the initial flow collecting bag 61. In other words, the initial flow of the blood collected from the donor through the blood collection needle 29 (collected initiate blood flow) is removed from the blood collection needle side first line 21a through the branch connector 21j and the fourth line 24 for collection in the initial flow collecting bag 61. As a result of this, the initial flow of the collected blood, which is highly probably infected with bacteria, can be easily removed or collected, whereby the mixing of bacteria into the blood components (platelets, plasma, etc.) separated from the collected blood is restrained, and safety is enhanced.

In addition, the blood stored in the initial flow collecting bag 61 can be recovered (sampling), for example, into a vacuum blood collection tube having a rubber stopper which is not shown.

In this case, after the clamp 91 is closed, the cap 66 of the holder 65 is detached, the vacuum blood collection tube is inserted into the holder 65 starting from the rubber stopper side thereof, and is pushed into the deepest portion of the holder 65, whereby the needle pipe 63 pierces through the rubber stopper. As a result of this, the blood stored in the initial flow collecting bag 61 flows through the tube 62 and is sucked into and recovered in the vacuum blood collection tube. After the collecting of the blood in the vacuum blood collection tube is finished, the vacuum blood collection tube is drawn out of the holder 65. In the case where the blood is to be collected into a plurality of vacuum blood collection tubes, the just-mentioned process is repeated.

The blood thus recovered into the vacuum blood collection tube(s) can be used, for example, in connection with biochemical test of serum, antibody tests concerning infectious viruses (e.g., AIDS, hepatitis, etc.) or the like.

In addition, the blood collection needle side first line 21a is equipped with a protector 94 between the blood collection needle 21 and the branch connector 21j. The protector 94 can be moved relative to the blood collection needle 21 toward the tip end side, from a position receded toward the base end side to a position for covering or housing the blood collection needle 21. After use, the protector 94 is moved toward the tip end side relative to the blood collection needle 21, and the, blood collection needle 21 is covered by the protector 94.

The plasma collecting bag (third container) 25 is a container for collecting or reserving plasma (second blood component). One end of the tube 49 is connected to the plasma collecting bag 25, and a branch connector 22d is provided at an intermediate portion of the tube 49. One end of the tube 50 is connected to the branch connector 22d, and the other end of the tube 50 is connected to the branch connector 21f.

One end of the tube 43 is connected to the branch connector 22b, and a branch connector 22c provided at the other end of the tube 43. One end of the tube 44 is connected to the branch connector 22c, and the other end of the tube 44 is connected to the plasma collecting bag 25.

In addition, the bubble sensor 33 is disposed along the tube 46 at an intermediate portion of the tube 46.

The plasma collecting bag 25 and the tubes 43, 44 constitute a plasma collecting branch line for collecting the plasma.

The platelet (platelet product) collecting bag 26 serving as a second container or a blood component collecting bag is a container for collecting (reserving) a platelet-containing plasma (first blood component) which has passed through a leukocyte (white blood cell) reduction filter 261. In the following description, the platelet-containing plasma (first blood component) will be referred to as "platelet concentrate", and the platelet concentrate collected or reserved in the platelet collecting bag 26 will be referred to as "platelet product".

One end of the tube 51 is connected to the platelet collecting bag 26, and the bag 28 is connected to the other end of the tube 51.

The air bag 27b is a container for temporarily storing or reserving air.

At the time of blood collection as described in more detail below, air (sterilized air) in the blood component collecting circuit 2, such as the blood reserving space 146 in the centrifugal separator 20, is transported into and stored in the air bag 27b. At the time of blood return (blood component return step), the air stored in the air bag 27b is transported and returned into the blood reserving space 146 in the centrifugal separator 20. As a result of this, predetermined blood components are returned to the donor.

One end of the tube 42 is connected to the branch connector 22b, and the other end of the tube 42 is connected to the air bag 27b.

The intermediate bag 27a (temporarily reserving bag), serving as a first container, is a container for temporarily reserving the platelet concentrate (first blood component). One end of the tube 45 is connected to the branch connector 22c, and the other end of the tube 45 is connected to the intermediate bag 27a.

In addition, one end of the tube 46 is connected to the intermediate bag 27a, and a branch connector 22e is connected to the other end of the tube 46. The other end of the above-mentioned tube 49 is connected to the branch connector 22e.

One end of the tube 47 is connected to the branch connector 22e, and the leukocyte reduction filter (blood cell separating filter) 261 for separating and reducing (removing) leukocyte (predetermined blood cells) from the platelet concentrate is disposed in an intermediate portion of the tube 47.

In addition, a branch connector 22g is provided at the other end of the tube 47. The other end of the tube 48, which is connected at its one end to the platelet collecting bag 26, is connected to the branch connector 22g.

A filter 22h, including a filter main body, which is provided with a vent filter, and a cap is disposed at a port of the branch connector 22g.

Here, the tubes 46, 47 constitute a supply tube for supplying the platelet concentrate from the intermediate bag 27a to the leukocyte reduction filter 261, whereas the tube 48 constitutes a discharge tube for discharging the platelet concentrate, after separation and reduction of the leukocytes, from the leukocyte reduction filter 261 (for supplying the platelet concentrate into the platelet collecting bag 26).

In other words, the tubes 46, 47, 48, the intermediate bag 27a, the leukocyte reduction filter 261 and the platelet collecting bag 26 constitute a filtration line for separating and reducing the leukocytes from the platelet concentrate.

The intermediate bag 27a, the leukocyte reduction filter 261 and the platelet collecting bag 26 are so arranged that, in the assembled state of the blood component collection apparatus 1, the leukocyte reduction filer 261 is located below the intermediate bag 27a, and, further, the platelet collecting bag 26 is located below the leukocyte reduction filter 261.

Examples of the leukocyte reduction filter 261 include a filter having a configuration in which a filter member composed of a layer or layers of a porous material such as woven fabric, non-woven fabric, mesh, foamed material, etc. of a synthetic resin such as polypropylene, polyester, polyurethane, polyamide, etc. is inserted in a casing (housing) provided with an inflow port and a discharge port (outflow port) respectively at both ends thereof.

The constituent materials of the tubes used for forming the first to fourth lines 21-24, the pump tubes 21g, 23a, and the other tubes 41-51, 62, 21h are each preferably polyvinyl chloride.

Where these tubes are made of polyvinyl chloride, sufficient pliability and flexibility can be obtained so that the tubes are easy to handle and are suitable for closing thereof by clamps or the like.

The materials constituting the branch connectors 21c, 21f, 21j, 22b, 22c, 22d, 22e, 22g can be the same as the constituent material just mentioned for the tubes.

It is preferable that the pump tubes 21g, 23g be constructed as tubes having sufficient strength so as not to be damaged even when pressed by the liquid feed pumps (e.g., roller pumps or the like) 11, 12 which will be described later are used.

Each of the plasma collecting bag 25, the platelet collecting bag 26, the intermediate bag 27a, the air bag 27b, the bag 28, and the initial flow collecting bag 61 can be in the form of a bag-like body produced by laying resin-made flexible sheet materials on each other and subjecting a peripheral edge portion of the sheet materials to fusing (heat fusing, high frequency fusing, ultrasonic fusing, or the like), adhesion with an adhesive, or the like. As described above, the air bag 27b and the intermediate bag 27a are formed integrally (united).

The material used to form the bags 25, 26, 27a, 27b, 28, 61 is preferably a soft polyvinyl chloride.

The sheet material used for forming the platelet collecting bag 26 is preferably a sheet material excellent in gas permeability for enhancing platelet conservation performance.

As examples of such a sheet material, polyolefin or DnDP plasticized polyvinyl chloride or the like is preferably used.

A primary portion of the blood component collecting circuit 2 described above is, for example, formed to be of a cassette type. To be more specific, the blood component collecting circuit 2 is provided with a cassette housing which partly accommodates and partly holds the lines (the first line 21, the second line 22, and the third line 23) and predetermined tubes, or, in other words, in which the lines and the tubes are partly fixed.

Both ends of the first tube 21g and both ends of the second tube 23a are fixed to the cassette housing, and the pump tubes 21g, 23g protrude from the cassette housing in the form of loops corresponding respectively to the liquid feed pumps (e.g., roller pumps or the like) 11, 12. Therefore, the first and second pump tubes 21g, 23g are easy to attach to the liquid feed pumps 11, 12, respectively. In addition, the passage opening/closing devices 81-87, which will be described later, and the like are disposed in the cassette housing.

The centrifugal separator 20 provided in the blood component collecting circuit 2 is usually called a centrifugal bowl, and separates blood into a plurality of blood components by centrifugal force.

As shown in FIG. 2, the centrifugal separator 20 has a pipe body 141 provided with the inflow port 143 at its upper end and extending in the vertical direction, and the hollow rotor 142 rotated around the pipe body 141 and sealed in a liquid-tight manner relative to an upper member 145 of the centrifugal separator 20.

The rotor 142 is provided with the annular blood reserving space 146 along the inside surface of the peripheral wall thereof. The blood reserving space 146 has such a shape that the inside and outside diameters are gradually reduced in the direction from the lower portion toward the upper portion in FIG. 2 (tapered shape). The lower portion of the blood reserving space 146 communicates with a lower end opening of the pipe body 141 through a substantially circular disk-shaped passage formed along a bottom portion of the rotor 142, and an upper portion of the blood reserving space 146 communicates with the discharge port (outflow port) 144. In the rotor 142, the inside volume of the blood reserving space 146 is, for example, about 100 to 350 mL, and the maximum inside radius of the rotor 142 measured from the axis of rotation is, for example, about 55 to 65 mm.

Such a rotor 142 is rotated under predetermined centrifugation conditions (rotating speed and rotating period) which are preliminarily set according to the centrifugal separator drive unit 10 provided in the blood component collection apparatus 1. The separation pattern of the blood in the rotor 142 (for example, the number of blood components into which the blood is separated) can be set by the centrifugation conditions.

In this embodiment, the centrifugation conditions are so set that the blood will be separated into a plasma layer 131, a buffy coat layer 132 and a red blood cell (erythrocyte) layer 133, in this order from the inner side toward the outer side in the blood reserving space 146 of the rotor as shown in FIG. 2.

The overall configuration of the blood component collection apparatus 1 shown in FIG. 1 will be described in more detail below. The blood component collection apparatus 1 comprises: the centrifugal separator drive unit 10 for rotating the rotor 142 of the centrifugal separator 20; the first liquid feed pump 11 disposed in an intermediate portion of the first line 21; the second liquid feed pump 12 disposed in an intermediate portion of the third line 23; the plurality of passage opening/closing devices 81, 82, 83, 84, 85, 86, 87 that are adapted to open and close the passages in the blood component collecting circuit 2 (the first line 21, the tube 42, the tube 44, the tube 45, the tube 47, the tube 49 and the tube 50); and the control unit (control means) 13 for controlling the centrifugal separator drive unit 10, the first liquid feed pump 11, the second liquid feed pump 12 and the plurality of passage opening/closing device 81-87.

Further, the blood component collection apparatus 1 comprises the turbidity sensor 14 mounted or disposed in the second line 22, the optical sensor 15 disposed in the vicinity of the centrifugal separator 20, the plurality of bubble sensors 31-36, and the weight sensor 16 for measuring the weight of the plasma, inclusive of the weight of the plasma collecting bag 25.

The control unit 13 includes two pump controllers for controlling the first liquid feed pump 11 and the second liquid feed pump 12, and the control unit 13 is in electrical connection with the first liquid feed pump 11 and the second liquid feed pump 12 respectively through the pump controllers.

A drive controller possessed by or associated with the centrifugal separator drive unit 10 is also in electrical connection with the control unit 13.

The passage opening/closing devices 81-87 are also in electrical connection with the control unit 13.

In addition, the turbidity sensor 14, the optical sensor 15, the weight sensor 16, and the bubble sensors 31-36 are in electrical connection with the control unit 13.

The control unit 13 is composed of, for example, a microcomputer. Detection signals from the turbidity sensor 14, the optical sensor 15, the weight sensor 16, and the bubble sensors 31-36 are respectively inputted to the control unit 13 on occasion or at certain intervals.

Based on the detection signals from the turbidity sensor 14, the optical sensor 15, the weight sensor 16, and the bubble sensors 31-36, and according to a preset program, the control unit 13 controls the operations of the individual parts of the blood component collection apparatus 1. More specifically, the control unit 13 controls the rotation, stopping, and rotating direction (normal rotation/reverse rotation) of each of the liquid feed pumps 11, 12, and controls, as required, the opening and closing of each of the passage opening/closing devices 81-87 and the operation of the centrifugal separator drive unit 10.

The first passage opening/closing device 81 is provided for opening and closing the passage in the first line 21 at a position on the blood collection needle 29 side relative to the first pump tube 21g, specifically, at a position between the branch connector 21f and the chamber 21d.

The second passage opening/closing device 82 is provided for opening and closing the passage in the tube 50. The third passage opening/closing device 83 is provided for opening and closing the passage in the tube 44. The fourth passage opening/closing device 84 is provided for opening and closing the passage in the tube 45. The fifth passage opening/closing device 85 is provided for opening and closing the passage in the tube 42. The sixth passage opening/closing device 86 is provided for opening and closing the passage in the tube 49. The seventh passage opening/closing device 87 is provided for opening and closing the passage in the tube 47.

The passage opening/closing devices 81-87 have insertion portions in which the first line 21 and the tubes 50, 44, 45, 42, 49, 47 can be inserted respectively, and a clamp operated by a drive source such as solenoid, electric motor, cylinder (hydraulic or pneumatic), etc. is provided at each of the insertion portions. A solenoid clamp operated by a solenoid is preferably used as the clamp.

These passage opening/closing devices (clamps) 81-87 are respectively operated based on signals from the control unit 13.

As shown in FIG. 2, the centrifugal separator drive unit 10 has a housing 201 for housing the centrifugal separator 20, a base portion 202, a motor 203 as a drive source, and a circular disk-like fixing base 205 for holding the centrifugal separator 20.

The housing 201 is mounted on and fixed to an upper portion of the base portion 202. In addition, the motor 203 is fixed to the lower surface of the housing 201 by bolts 206 through a spacer 207.

The fixing base 205 is fitted over a tip end portion of a rotary shaft 204 of the motor 203, is coaxial with the rotary shaft 204 and is rotated unitarily as one body with the rotary shaft 204. The fixing base 205 is provided in its upper portion with a recess in which a bottom portion of the rotor 142 is fitted.

The upper member 145 of the centrifugal separator 20 is fixed to the housing 201 by a fixing member.

In the centrifugal separator drive unit 10 described above, when the motor 203 is driven, the fixing base 205 and the rotor 142 fixed thereto are rotated together, for example at a rotating speed of about 3000 to 6000 rpm.

The optical sensor 15 is disposed at a side portion (the left side in FIG. 2) of the housing 201. The optical sensor 15 is so configured as to cast light toward the blood reserving space 146 and to receive the reflected light.

The optical sensor 15 radiates or casts light (e.g., a laser beam) from a light casting portion 151, and receives at a light receiving portion 152 the light reflected on a reflective surface 147 of the rotor 142. The light received at the light receiving portion 152 is converted into an electric signal according to the amount of light received.

Here, the optical sensor 15 has a reflective plate 153 which has a reflective surface on one side thereof and changes the optical path. The light radiated from the light casting portion 151 is radiated onto the reflective surface 147 through the reflective plate 153, and the light reflected on the reflective surface 153 is received by the light receiving portion 152 via the reflective plate 153.

In this instance, the cast light and the reflected light are each transmitted through the blood components in the blood reserving space 146. According to the position of an interface between the blood components (in this embodiment, the interface B between the plasma layer 131 and the buffy coat layer 132), the presence ratio between the blood components at the position through which the cast light and the reflected light are transmitted differs, so that the transmittance therethrough varies. This ensures that the amount of light received at the light receiving portion 152 is varied or changed, and the variation can be detected as a change in the output voltage of the light receiving portion 152.

The optical sensor 15 can thus detect the position of the interface between the blood components based on the change in the amount of light received by the light receiving portion 152.

The interface between the blood components detected by the optical sensor 15 is not limited to the interface B. For example, the interface between the buffy coat layer 132 and the red blood cell layer 133 may be detected.

Here, the layers 131-133 in the blood reserving space 146 differ in color according to the blood components; particularly, the red blood cell layer 133 appears red due to the color of the red blood cells. Therefore, from the viewpoint of enhancing the accuracy of the optical sensor 15, there is a preferable range for the wavelength of the cast light. The wavelength range is not particularly limited but is preferably about 600 to 900 nm, more preferably about 750 to 800 nm.

The turbidity sensor 14 detects the turbidity of a fluid flowing in the second line 22, and outputs a voltage according to the turbidity. A lower voltage is outputted when the turbidity is higher, and a higher voltage is outputted when the turbidity is lower.

By virtue of the turbidity sensor 14, it is possible to detect, for example, a variation in the concentration of platelets in the plasma flowing in the second line 22, the mixing of red blood cells into the plasma, or the like.

In addition, by virtue of the bubble sensor 34, it is possible to detect, for example, replacement of air by plasma in the fluid flowing in the second line 22, or the like.

As each of the turbidity sensor 14 and the bubble sensors 31-36, it is possible to use, for example, an ultrasonic sensor, an optical sensor, an IR sensor or the like.

A preferred example of the pump used for the first liquid feed pump 11 mounted in the first pump tube 21g and the second liquid feed pump 12 mounted in the second pump tube 23a is a non-blood-contact type pump such as a roller pump.

With regard to the first liquid feed pump (blood pump) 11, a pump adapted to feed blood in both directions is preferably used. Specifically, a roller pump adapted to carry out normal rotation and reverse rotation is preferably used.

The second liquid feed pump 12 is a supply means for supplying an anticoagulant into a predetermined passage in the blood component collecting circuit 2, in other words for adding an anticoagulant to the blood. In the blood component collection apparatus 1, to begin with, a priming operation is performed in which the anticoagulant is fed or supplied from the passage of the third line 23 (anticoagulant feeding line) and through the branch connector 21c until it flows into the chamber 21d in the blood collection needle side first line 21a, by operating the second liquid feed pump (supply means) 12 under the condition in which the clamp 91 is open and the clamps 92, 93 are closed. As a result of this, air in the third line 23 and in the passage of the blood collection needle side first line 21a ranging from the branch connector 21c to the immediate upstream side of the chamber 21d is transferred into the chamber 21d and the passage of the blood collection needle side first line 21a on the downstream side of the chamber 21d.

Next, an initial flow collecting operation is carried out in which the initial flow of the blood collected from a donor (collected initiate blood flow) is introduced through the passage of the blood collection needle side first line 21a ranging from the blood collection needle 29 to the branch connector 21j into the fourth line 24 and is collected into the initial flow collecting bag 61, under the condition where the clamps 91 and 92 are open and the clamp 93 is closed. As a result, air in the passage of the blood collection needle side first line 21a ranging from the blood collection needle 29 to the branch connector 21j and in the passage of the fourth line 24 is transferred into the initial flow collecting bag 61.

After the priming operation and the initial flow collecting operation are carried out, air in the passage of the blood collection needle side first line 21a ranging from the branch connector 21j to the branch connector 21c is not transferred but stays there, and so air is intermediately present between the collected initiate blood flow and the anticoagulant in the passage of the blood collection needle side first line 21a. That is, an air layer is formed between the collected initiate blood flow and the anticoagulant in the passage of the blood collection needle side first line 21a.

This air layer ensures that contact between the collected initiate blood flow and the anticoagulant is inhibited, and the mixing of the anticoagulant into the collected initiate blood flow can be prevented. Thus, the collected initiate blood flow reserved in the initial flow collecting bag 61 can be used as blood to be tested. Simultaneously, since the mixing of the collected initiate blood flow into the coagulant can be prevented, it is possible to prevent bacteria from mixing into the platelets (platelet product) collected into the platelet collecting bag 26 or into the plasma (plasma product and raw material plasma) collected into the plasma collecting bag 25.

By virtue of the construction and operation described above, an air layer is formed by not completely filling the passage of the blood collection needle side first line 21a between the branch connector 21c and the branch connector 21j with the anticoagulant at the time of the priming operation. To be more specific, in the condition where the priming has been completed, the gas-liquid separation surface (interface) between the anticoagulant and the air layer in the passage of the blood collection needle side first line 21a is located on the branch connector 21j side relative to the branching center (central portion) of the branch connector 21c, i.e., between the branching center (central portion) of the branch connector 21c and the branching center (central portion) of the branch connector 21j. In this embodiment, since the priming operation is carried out in the condition where the clamp 93 is closed, the gas-liquid separation surface is located in the vicinity of the branching center of the branch connector 21c. In addition, in this embodiment, since the initial flow collecting operation is performed in the condition where the clamp 93 is closed, the gas-liquid separation surface (interface) between the collected initiate blood flow (blood) and the air layer in the passage of the blood collection needle side first line 21a is located between the branching center of the branch connector 21c and the branching center of the branching connector 21j, and in the vicinity of the branching center of the branch connector 21j.

After the priming operation and the initial flow collecting operation are carried out, i.e., after a predetermined amount of the collected initiate blood flow is collected into the initial flow collecting bag 61 via (through) the fourth line 24, an anticoagulant supplying operation is conducted in which the anticoagulant is supplied from the passage of the third line (anticoagulant feeding line) 23 toward the fourth line (initial flow collecting line) 24 through the branch connector 21c and the branch connector 21j, by operating the second liquid feed pump 12 in the condition where the clamps 91 and 93 are open and the clamp 92 is closed. By virtue of the anticoagulant supplying operation, the air layer between the collected initiate blood flow and the anticoagulant is transferred from the blood collection needle side initial flow 21a into the fourth line 24. The anticoagulant supplying operation is carried out until the anticoagulant flows into the fourth line 24 while the air layer does not flow into the initial flow collecting bag 61.

This ensures that the air layer is removed from the blood collection needle side first line 21a, and it is possible to prevent the blood not containing the anticoagulant from stagnating in the fourth line 24 and the branch connector 21j and coagulating there.

Here, the length La of the blood collection needle side first line 21a between the branching center of the branch connector 21c and the branching center of the branch connector 21j is preferably set to be smaller than the length Lb of the fourth line 24 between the branching center of the branch connector 21j and the initial flow collecting bag 61. In other words, the length Lc of the air layer between the collected initiate blood flow and the anticoagulant in the passage of the blood collection needle side first line 21a, measured along the direction (longitudinal direction) of the blood collection needle side first line 21a, is preferably set to be smaller than the length Lb of the fourth line 24 between the branching center of the branch connector 21j and the initial flow collecting bag 61.

The reason for the above setting is to prevent the air in the air layer from flowing into the initial flow collecting bag 61 at the time of supplying the anticoagulant into the fourth line 24 after a predetermined amount of the collected initiate blood flow is collected. If the air in the air layer flows into the initial flow collecting bag 61, the pressure inside the initial flow collecting bag 61 becomes so high that, at the time of recovering the blood in the initial flow collecting bag 61 into the vacuum blood collection tube, the amount of the blood recovered into the vacuum blood collection tube would be greater than a planned amount.

At least a part of the blood collection needle side first line 21a between the branch connector 21c and the branch connector 21j is composed of a tube. In this embodiment, as above-described, the whole part of the blood collection needle side first line 21 a between the branch connector 21c and the branch connector 21j is composed of a tube. If the length of the clamp 93 as mounted on the tube, measured along the direction (longitudinal direction) of the tube, is Ld, then the length Le of the tube is preferably greater than Ld+30 mm, more preferably greater than Ld+60 mm.

This setting makes it possible to mount the clamp 93 onto the tube easily and assuredly, and to carry out in a reliable manner the operations of opening and closing the clamp 93.

As for specific numerical values, considering the aforementioned parameters, the length La is preferably about 60 to 120 mm, more preferably about 70 to 110 mm.

In addition, the length Le of the above-mentioned tube is preferably about 40 to 110 mm, more preferably about 50 to 90 mm.

Now, the operation of the blood component collection apparatus 1 will be described below.

First, a platelet collecting operation (blood component collecting operation) using the blood component collection apparatus 1 will be described.

The blood component collection apparatus 1, under the control of the control unit 13, is operated to perform the platelet collecting operation (blood component collecting operation) which includes a first plasma collection step, a constant-speed plasma circulation step, a second plasma collection step, an accelerated plasma recirculation step, a third plasma collection step, a platelet collection step, and a blood return step (blood component return step).

A blood component collection step is composed of the first plasma collection step, the constant-speed plasma circulating step, the second plasma collection step, the accelerated plasma circulating step, the third plasma collection step, and the platelet collection step. By conducting the blood component collection step, plasma is collected in the plasma collecting bag 25, and platelet concentrate are collected into the intermediate bag 27a. In addition, by performing the blood return step, the blood components remaining in the blood reserving space 146 of the rotor 142 of the centrifugal separator 20 (residual blood components, mainly red blood cells and leukocytes) are discharged through the inflow port 143 of the centrifugal separator 20 and returned through the first line 21 (blood collection needle 29) into the donor. In blood component collection, the platelet collecting operation including the blood component collection step and the blood return step is carried out at least once (one cycle). Incidentally, the platelet collecting operation is normally conducted a plurality of times (a plurality of cycles).

The platelet collecting operation can be conducted by use of the method described, for example, in U.S. Patent Application Publication No. 2004/0112808 A1, though the circuit configuration described in that patent is a little different from the circuit configuration described here.

In addition, concurrently with or after completion of the final cycle of the platelet collecting operation, the blood component collection apparatus 1 under the control by the control unit 13 is operated to carry out a filtration operation (filtration step) in which the platelet concentrate temporarily collected (reserved) in the intermediate bag 27a are supplied into the leukocyte reduction filter 261 so as to filter the platelet concentrate, namely to separate and remove the leukocytes from the platelet concentrate.

In the filtration operation, the seventh passage opening/closing means 87 is opened. This ensures that the platelet concentrate in the intermediate bag 27a is transferred through the tubes 46 and 47, the leukocyte reduction filter 261 and the tube 48 into the platelet collecting bag 26, under a head (gravity). In this instance, the platelet concentrate mostly pass through the filter member in the leukocyte reduction filter, whereas the leukocytes are trapped by the filter member. Therefore, the removal rate for the leukocytes in the platelet product can be made extremely high.

It is to be understood that the transfer of the platelet concentrate from the inside of the intermediate bag 27a into the platelet collecting bag 26 may be conducted by use of a pump.

In addition, the priming operation (priming step), an operation (step) of removing (collecting) the collected initiate blood flow, and an operation (step) of supplying an anticoagulant into the fourth line 24 are carried out in this order, prior to the first cycle of the platelet collecting operation.

Now, the steps ranging from the priming step to the step of supplying the anticoagulant into the fourth line 24 (the step preceding the first cycle of the platelet collecting operation) will be described below.

[1] First, a condition is established where the clamp 91 is open and the clamps 92, 93 are closed, and the third line 23 and the passage of the blood collection needle side first line 21a of the first line 21 ranging from the branch connector 21c to the chamber 21d are primed with the anticoagulant.

Specifically, the second liquid feed pump 12 is operated under the control of the control unit 13. As a result, the anticoagulant flows from the third line 23 through the branch connector 21c and flows in the first line 21 toward the chamber 21d, whereby the third line 23 and the passage of the first line 21 ranging from the branch connector 21c to the chamber 21d are primed with the anticoagulant. When the anticoagulant is detected by all the bubble sensors 31, 35, 36, the priming is completed, and the operation of the second liquid feed pump 12 is stopped.

[2] Next, a blood vessel of a donor is punctured by the blood collection needle 29, and the clamp 92 is opened.

As a result, the initial flow of the blood collected from the donor through the blood collection needle 29 (collected initiate blood flow), under the venous blood pressure of the donor and/or a head (gravity), flows through the blood collection needle 29, the blood collection needle side first line 21a, the branch connector 21j and the fourth line 24, to be introduced (collected) into the initial flow collecting bag 61. In this case, as above-described, an air layer is formed in the passage of the blood collection needle side first line 21a between the branch connector 21c and the branch connector 21j, namely, between the collected initiate blood flow and the anticoagulant in the passage of the blood collection needle side first line 21a. Due to the presence of the air layer, contact between the collected initiate blood flow and the anticoagulant is inhibited, and the anticoagulant can be prevented from mixing into the collected initiate blood flow.

When a predetermined amount of the blood is collected in the initial flow collecting bag 61, the clamp 92 is closed, whereby collection of the collected initiate blood flow is finished.

[3] Subsequently, the clamp 93 is opened, and then the blood component collection apparatus 1 supplies the anticoagulant into the fourth line 24 through the third line 23, the branch connector 21c and the branch connector 21j.

Specifically, the second liquid feed pump 12 is operated under the control of the control unit 13. In this case, the second liquid feed pump 12 is rotated by a predetermined number of times (until the anticoagulant flows into the fourth line 24 while the air layer does not flow into the initial flow collecting bag 61).

As a result, the anticoagulant flows through the branch connector 21c, the blood collection needle side first line 21a, the branch connector 21j and the fourth line 24 (is supplied into the fourth line 24), whereby the third line 23, the passage of the first line 21 ranging from the branch connector 21c to the branch connector 21j, and the passage of the fourth line 24 ranging from the branch connector 21j to an intermediate portion, are filled (washed) with the anticoagulant.

It is to be noted that this step [3] and the steps [1] and [2] are carried out only before the first cycle.

In addition, this step [3] may be conducted by an operator manually rotating the second liquid feed pump 12.

When this step [3] is finished, the clamp 91 is closed, the clamp 92 is opened, and the next step (the first cycle of the platelet collecting operation) is started. A detailed description of the subsequent steps is omitted here because, as noted above, such steps can be carried out in a manner similar to that described in the aforementioned patent.

As has been described above, according to this blood component collection apparatus 1, due to the presence of the fourth line 24, the initial flow of the blood collected (collected initiate blood flow) which is highly probably infected with bacteria can be easily removed at the time of blood collecting. This ensures that mixing of the bacteria into the collected platelet concentrate, the platelet product or the plasma is restrained, and safety is enhanced.

In addition, the collected initiate blood flow thus removed can be reserved in the initial flow collecting bag 61.

Because the air layer is formed between the collected initiate blood flow and the anticoagulant in the passage of the blood collection needle side first line 21a after the priming operation and the initial flow collecting operation are carried out, the contact between the collected initiate blood flow and the anticoagulant is inhibited, and mixing of the anticoagulant into the collected initiate blood flow can be prevented, by the air layer. As a result, the collected initiate blood flow reserved in the initial flow collecting bag 61 can be used as blood to be tested.

In addition, since the contact between the collected initiate blood flow and the anticoagulant is inhibited, it is possible to prevent bacteria from mixing into the platelets (platelet product) collected in the platelet collecting bag 26 or into the plasma (plasma product or raw material plasma for a plasma fractional product) collected in the plasma collecting bag 25.

When the air layer is transferred from the blood collection needle side first line 21a into the fourth line 24 by performing the anticoagulant supplying operation after a predetermined amount of the collected initiate blood flow is removed (collected), the anticoagulant is supplied through the third line 23, the branch connector 21c and the branch connector 21j into the fourth line 24. It is thus possible to obviate the possibility that the blood not containing the anticoagulant may stagnate in the fourth line 24 and the branch connector 21j and coagulate there. This ensures that blood component collection can be performed safely and assuredly, without increasing the burden on the donor.

In addition, since the blood component collection can be conducted securely, the merit of the blood component collection that the blood collecting interval is shorter than that in the case of whole blood collecting would not be spoiled.

In the blood component collection apparatus 1, leukocytes are separated and removed by the leukocyte reduction filter 261 from the platelet concentrate separated and collected from a blood. It is thus possible to obtain a platelet product with extremely slight mixing of leukocytes therein.

The principles and preferred embodiment have been described in the foregoing specification, but the invention which is intended to be protected is not to be construed as limited to the particular embodiment disclosed.

It is to be noted, for example, that the present invention is applicable not only to obtaining a platelet product and a plasma product (or a raw material plasma for a plasma fractional product) but also, for example, for obtaining either one of a platelet product and a plasma product from blood. In other words, consistent with the disclosed apparatus and method, the blood component collected into the blood component collecting bag may be either one of platelets (platelet concentrate) and plasma.

The present invention is also applicable obtaining a red blood cell product, a leukocyte product or the like from a blood. In other words, consistent with the disclosed apparatus and method, the blood component collected into the blood component collecting bag is not limited to platelets (the platelet concentrate) or plasma, and may be, for example, red blood cells (concentrated red blood cells), leukocytes (concentrated leukocytes) or the like.

In addition, the blood cells separated and removed by the blood cell reduction (separation) filter are not limited to leukocytes.

The optical sensor is not limited to the illustrated and described sensor as, for example, a line sensor or the like can also be adopted.

It is also to be understood that the blood separator is not limited to the centrifugal-type separator described above and illustrated in the drawing figure. For example, a membrane-type separator or the like may also be employed.

The system of the blood component collection apparatus according is not limited to the intermittent system as, for example, a continuous system may also be utilized.

It is thus to be understood that the embodiment described herein is to be regarded as illustrative rather than restrictive. Variations and changes may be made by others (including additional features and steps), and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A blood component collection apparatus for separating blood from a donor so as to collect a predetermined blood component, comprising:
   a blood collection needle for collecting blood from a donor;
   a blood separator for separating said predetermined blood component from said blood collected by said blood collection needle;
   a blood component collecting bag for collecting said predetermined blood component separated by said blood separator,
   a blood line connecting said blood collection needle and an inflow port of said blood separator, said blood line being provided with a first branched portion and a second branched portion between said blood collection needle and said first branched portion,
   an initial flow collecting line branched from the second branched portion to collect an initial flow of said blood collected from said donor, and
   an anticoagulant feeding line branched from the first branched portion to feed an anticoagulant;
   supply means for adding said anticoagulant to said blood collected by said blood collection needle;
   an air containing space intermediately present between said anticoagulant and said blood in a passage of said blood line after both a priming operation is performed in which said anticoagulant is supplied from said anticoagulant feeding line toward a blood separator side of said blood line through said first branched portion by operating said supply means and an initial flow collecting operation is performed in which said initial flow of said blood is supplied to said initial flow collecting line; and
   an initial flow collecting bag provided in said initial flow collecting line so as to reserve said initial flow of said blood, wherein the length of a portion of said blood line between said first branched portion and said second branched portion is smaller than the length of a portion of said initial flow collecting line between said second branched portion and said initial flow collecting bag.

2. The blood component collection apparatus according to claim 1, further comprising:
   detection means for detecting a liquid present in said blood line between said first branched portion and said blood separator; and
   said priming operation is performed until said anticoagulant is detected by said detection means.

3. The blood component collection apparatus according to claim 1, further comprising:
   a first clamp adapted to open and close a passage of said initial flow collecting line;
   a second clamp adapted to open and close a passage of said blood line between said blood collection needle and said second branched portion; and
   a third clamp adapted to open and close a passage of said blood line between said first branched portion and said second branched portion.

4. The blood component collection apparatus according to claim 1, wherein an anticoagulant supplying operation for supplying said anticoagulant from said anticoagulant feeding line toward said initial flow collecting line through said first branched portion and said second branched portion is performed by operating said supply means after said priming operation and said initial flow collecting operation are performed, whereby said air containing space is transferred from said blood line into said initial flow collecting line.

5. The blood component collection apparatus according to claim 1, wherein the length of the air containing space between said anticoagulant and said blood as measured along said blood line is smaller than the length of a portion of said initial flow collecting line between said second branched portion and said initial flow collecting bag.

6. The blood component collection apparatus according to claim 1, wherein:
   at least a part of a portion of said blood line between said first branched portion and said second branched portion is comprised of a tube with a passage;
   said tube is provided with a clamp adapted to open and close the passage inside said tube; and
   a length of said tube is greater than Ld+30 mm, where Ld is the length of said clamp mounted on said tube as measured along said tube.

7. The blood component collection apparatus according to claim 1, wherein said supply means is a liquid feed pump disposed in said anticoagulant feeding line.

8. The blood component collection apparatus according to claim 1, performing at least one cycle of a blood component collecting operation including a blood component collection step for separating said predetermined blood component from other blood components in said collected blood and collecting said predetermined blood component, and a blood component return step for returning the other blood components.

9. A blood component collection apparatus for separating blood from a donor so as to collect a predetermined blood component, comprising:
   a blood collection needle for collecting blood from a donor;
   a blood separator which separates said predetermined blood component from said blood collected by said blood collection needle;
   a blood component collecting bag for collecting said predetermined blood component separated by said blood separator;
   a blood line connecting said blood collection needle and an inflow port of said blood separator, said blood line being provided with a first branched portion and a second branched portion, said second branched portion being positioned between said blood collection needle and said first branched portion, and
   an anticoagulant feeding line to feed an anticoagulant, the anticoagulant feeding line comprising one end branching from the first branched portion of the blood line;
   an initial flow collecting line comprising one end branching from the second branched portion; and
   the first and second branched portions of the blood line being spaced apart from one another along the blood line to provide an air space in the blood line between the anticoagulant and the blood in the blood line after a priming operation is performed in which the anticoagulant is supplied into the blood line through the anticoagulant feeding line and the first branched portion and after an initial flow collecting operation is performed in which the initial flow of the blood from the donor is supplied to the initial flow collecting line through the blood line and the second branched portion;
   wherein an opposite end of the initial flow collecting line is connected to an initial flow collecting bag, the length of a portion of said blood line between said first branched portion and said second branched portion is smaller than the length of a portion of said initial flow collecting line between said second branched portion and said initial flow collecting bag.

10. The blood component collection apparatus according to claim 9, further comprising detection means for detecting a liquid present in said blood line between said first branched portion and said blood separator.

11. The blood component collection apparatus according to claim 9, further comprising a clamp positioned along the blood line between the first and second branched portions to open and close the blood line.

12. The blood component collection apparatus according to claim 9, further comprising a clamp positioned along the blood line between the second branched portion and the blood collection needle to open and close the blood line.

13. The blood component collection apparatus according to claim 9, further comprising a clamp positioned along the initial flow collecting line between the second branched portion and the initial flow collecting bag.

* * * * *